US011179542B2

(12) United States Patent
Kullas et al.

(10) Patent No.: US 11,179,542 B2
(45) Date of Patent: Nov. 23, 2021

(54) IMPLANTABLE PROSTHESIS FOR FISTULA REPAIR

(71) Applicant: C.R. Bard, Inc., Murray Hill, NJ (US)

(72) Inventors: Karen E. Kullas, Berkley, MA (US); Tami L. Rathbun, Exeter, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 598 days.

(21) Appl. No.: 16/110,825

(22) Filed: Aug. 23, 2018

(65) Prior Publication Data

US 2018/0361113 A1 Dec. 20, 2018

Related U.S. Application Data

(62) Division of application No. 14/131,641, filed as application No. PCT/US2011/043320 on Jul. 8, 2011, now Pat. No. 10,080,863.

(51) Int. Cl.
*A61M 25/04* (2006.01)
*A61M 25/00* (2006.01)
(Continued)

(52) U.S. Cl.
CPC ..... *A61M 25/0017* (2013.01); *A61B 17/0057* (2013.01); *A61M 25/0023* (2013.01);
(Continued)

(58) Field of Classification Search
CPC .......... A61B 17/0057; A61B 17/06166; A61B 2017/00004; A61B 2017/00641;
(Continued)

(56) References Cited

U.S. PATENT DOCUMENTS 4,778,465 A    10/1988   Wilkins
4,790,309 A    12/1988   Becker
(Continued)

FOREIGN PATENT DOCUMENTS

CA            2342480 A1    9/2002
WO    WO 96/29043 A1    9/1996
(Continued)

OTHER PUBLICATIONS

International Search Report and Written Opinion for International application No. PCT/US2011/043320, dated Nov. 16, 2011.
(Continued)

*Primary Examiner* — Kai H Weng
(74) *Attorney, Agent, or Firm* — Wolf, Greenfield & Sacks, P.C.

(57) ABSTRACT

An implantable prosthesis is provided for repairing a fistula, such as an anal fistula. The prosthesis or fistula repair device may include a body with a shape configured for placement in the fistula. The prosthesis may also include an anchor or base that is located at one or both ends of the body to facilitate anchoring the prosthesis in position. The prosthesis may include one or more channels to create one or more pathways for drainage and/or irrigation of the fistula. The channel may have a relatively uniform dimension along its length or a tapered shape that increases along its length. The prosthesis may have an adjustable length for accommodating fistula tracts of varying lengths. The prosthesis may include elongated body segments that provide a wicking or capillary function to facilitate drainage of the fistula tract.

20 Claims, 14 Drawing Sheets

(51) Int. Cl.
  *A61B 17/00* (2006.01)
  *A61B 17/06* (2006.01)
(52) U.S. Cl.
  CPC ....... *A61M 25/04* (2013.01); *A61B 17/06166* (2013.01); *A61B 2017/00004* (2013.01); *A61B 2017/00641* (2013.01); *A61B 2017/00654* (2013.01); *A61B 2017/00676* (2013.01); *A61B 2017/00884* (2013.01); *A61B 2017/00893* (2013.01); *A61B 2217/005* (2013.01); *A61M 2025/006* (2013.01)
(58) Field of Classification Search
  CPC ........... A61B 2017/00654; A61B 2017/00676; A61B 2017/00884; A61B 2017/00893; A61B 2217/005; A61M 2025/006; A61M 25/0017; A61M 25/0023; A61M 25/04
  See application file for complete search history.

(56) References Cited

U.S. PATENT DOCUMENTS

| | | | |
|---|---|---|---|
| 5,116,370 A | 5/1992 | Foglietti | |
| 5,171,321 A | 12/1992 | Davis | |
| 5,300,120 A | 4/1994 | Knapp et al. | |
| 5,356,429 A | 10/1994 | Seare | |
| 5,836,912 A | 11/1998 | Kusleika | |
| 6,497,609 B1 | 12/2002 | Cobbs | |
| 6,974,473 B2 | 12/2005 | Barclay et al. | |
| 10,080,863 B2 | 9/2018 | Kullas et al. | |
| 2001/0005784 A1 | 6/2001 | Righetti | |
| 2002/0165479 A1* | 11/2002 | Wilk | A61F 2/064 604/8 |
| 2005/0159776 A1 | 7/2005 | Armstrong | |
| 2007/0088445 A1 | 4/2007 | Patel et al. | |
| 2007/0129757 A1 | 6/2007 | Armstrong | |
| 2007/0179507 A1 | 8/2007 | Shah | |
| 2007/0198059 A1 | 8/2007 | Patel et al. | |
| 2007/0250081 A1* | 10/2007 | Cahill | A61B 17/0057 606/151 |
| 2008/0004657 A1 | 1/2008 | Obeiiller et al. | |
| 2008/0208358 A1 | 8/2008 | Bellamkonda et al. | |
| 2008/0245374 A1 | 10/2008 | Agnew | |
| 2009/0012558 A1 | 1/2009 | Chen et al. | |
| 2009/0054927 A1 | 2/2009 | Agnew | |
| 2009/0069843 A1 | 3/2009 | Agnew | |
| 2009/0099647 A1* | 4/2009 | Glimsdale | A61B 17/12113 623/1.35 |
| 2009/0118836 A1 | 5/2009 | Cordaro | |
| 2009/0125119 A1 | 5/2009 | Obeiiller et al. | |
| 2009/0326577 A1* | 12/2009 | Johnson | A61B 17/0057 606/213 |
| 2010/0137999 A1 | 6/2010 | Shohat | |
| 2010/0228184 A1 | 9/2010 | Mavani et al. | |
| 2010/0241162 A1 | 9/2010 | Obermiller et al. | |
| 2010/0249828 A1 | 9/2010 | Mavani et al. | |
| 2010/0249830 A1 | 9/2010 | Nelson | |
| 2010/0331612 A1 | 12/2010 | Lashinski et al. | |
| 2011/0054520 A1 | 3/2011 | Deal et al. | |
| 2011/0060362 A1 | 3/2011 | Patel et al. | |
| 2012/0035644 A1 | 2/2012 | Eskaros et al. | |
| 2013/0211519 A1 | 8/2013 | Dempsey | |
| 2014/0303603 A1 | 10/2014 | Kullas et al. | |
| 2014/0309737 A1 | 10/2014 | Kullas et al. | |

FOREIGN PATENT DOCUMENTS

| | | | |
|---|---|---|---|
| WO | WO 2007/011443 A2 | 1/2007 | |
| WO | WO 2007/084285 A2 | 7/2007 | |
| WO | WO 2007/149989 A2 | 12/2007 | |
| WO | WO 2009/070686 A1 | 6/2009 | |
| WO | WO 2010/019292 A1 | 2/2010 | |
| WO | WO 2010/028300 A1 | 3/2010 | |

OTHER PUBLICATIONS

International Search Report and Written Opinion for International application No. PCT/US2011/043332, dated Nov. 15, 2011.
Extended European Search Report for European Patent Application No. 11869374.6, dated Nov. 6, 2014.
Communication pursuant to Article 94(3) EPC for European Patent Application No. 11869374.6, dated Jan. 13, 2016.
Extended European Search Report for EP17186681.7, dated Jan. 11, 2018.
[No Author Listed] Instructions for Use For: Gore Bio-A Fistula Plug, W. L. Gore and Associates, Inc. Jun. 2009, 5 pages.
[No Author Listed] The Next Generation of Anal Fistula Repair, W. L. Gore and Associates, Inc. Nov. 2009, 4 pages.

* cited by examiner

IMPLANTABLE PROSTHESIS FOR FISTULA REPAIR

RELATED APPLICATIONS

This application is a divisional of U.S. application Ser. No. 14/131,641, filed Jun. 30, 2014, which is a 371 U.S. National Stage application of International Application No. PCT/US2011/043320, filed Jul. 8, 2011. The entire contents of these applications are incorporated herein by reference in their entirety.

FIELD

The present invention relates to an implantable prosthesis, and more particularly to an implantable prosthesis for repairing a fistula, such as an anal fistula.

BACKGROUND

An anal fistula is an abnormal passage or connection between the anal canal, including the colon, bowel or rectum, and the perianal skin. Contaminants or waste matter, such as excrement or feces, may pass through the fistula tract rather than passing naturally through the anal sphincter to exit the body.

An anal fistula may be treated by cleaning the fistula tract and inserting a seton, which may include a cord with a thread and a penrose drain, to maintain the fistula open for drainage. However, contamination or waste matter may not necessarily exit via the anal sphincter when treating the fistula with a seton.

It has been proposed to close an anal fistula using an anal fistula plug. Such plugs are configured to be fitted into and close the fistula so that contamination or waste matter is directed away from the fistula and naturally exits the body through the anal sphincter.

SUMMARY

An implantable prosthesis is provided for repairing a fistula that has a primary opening, a secondary opening and a fistula tract extending between the primary and secondary openings.

In one embodiment, the implantable prosthesis comprises an implantable body of biocompatible material that is adapted to extend along and approximate the fistula tract. The body includes first and second ends with a channel extending through the body to allow drainage of the fistula. At least a portion of the channel has an inner dimension that increases in a direction from the first end toward the second end.

In another embodiment, the implantable prosthesis comprises an implantable body of biocompatible material that is adapted to extend along and approximate the fistula tract. The body includes first and second ends with a channel extending through the body to allow drainage of the fistula. The body has an adjustable length to vary the distance between the first and second ends.

In a further embodiment, the implantable prosthesis comprises an implantable body of biocompatible material that is adapted to extend along and approximate the fistula tract. The body includes first and second ends with a channel extending through the body to allow drainage of the fistula. The prosthesis further comprises a first anchor located at the first end of the implantable body and adapted to be positioned at the primary opening of the fistula, and a second anchor located at the second end of the implantable body and adapted to be positioned at the secondary opening of the fistula. The first and second anchors are larger than the implantable body.

In another embodiment, the implantable prosthesis comprises an implantable body of biocompatible material including a plurality elongated body segments that are adapted to extend along the fistula tract. The elongated of body segments are adapted to wick fluid from the fistula. The prosthesis also comprises a base of biocompatible material that is located at a first end of the body with the plurality of elongated body segments extending away from the base. The base is adapted to be positioned at the primary opening of the fistula and has an opening therethrough to allow drainage and/or irrigation of the fistula.

In a further embodiment, a method is provided for repairing a fistula that includes a fistula tract extending from a primary opening to a secondary opening. The method comprises an act of implanting a prosthesis in a fistula tract, the prosthesis including an implantable body of biocompatible material that is adapted to extend along and approximate the fistula tract. The body includes first and second ends with a channel extending through the body to allow drainage of the fistula. At least a portion of the channel has an inner dimension that increases in a direction from the first end toward the second end.

In another embodiment, a method is provided for repairing a fistula that includes a fistula tract extending from a primary opening to a secondary opening. The method comprises an act of implanting a prosthesis in a fistula tract, the prosthesis including an implantable body of biocompatible material that is adapted to extend along and approximate the fistula tract. The body includes a plurality of layers of biocompatible material arranged in a stacked configuration with each layer being in spaced relation to an adjacent layer. Each layer includes at least one opening to allow drainage through the body.

DETAILED DESCRIPTION

Figure 1:
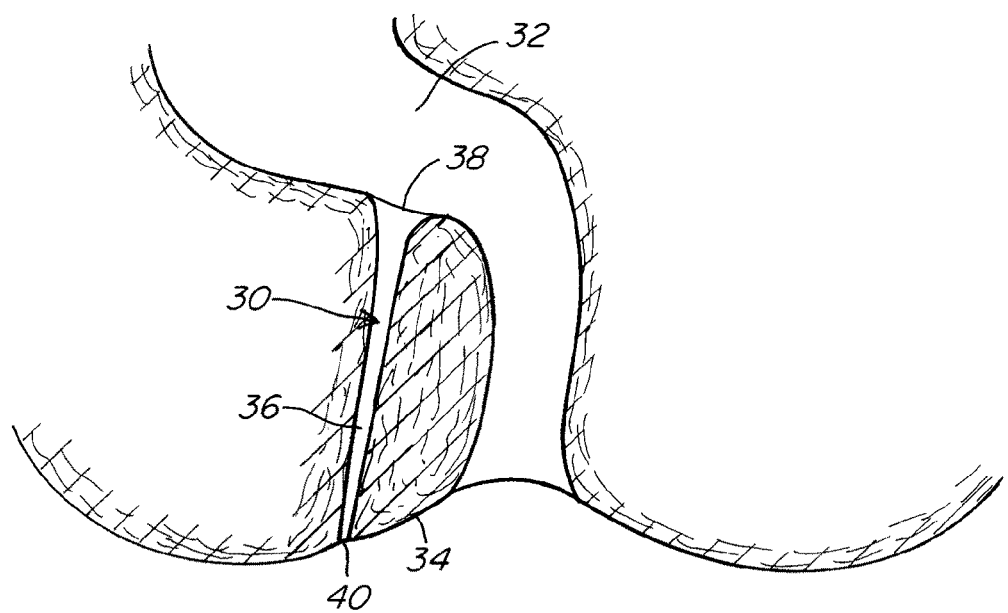
FIG. 1 is a schematic cross-sectional view of an anal fistula.

An implantable prosthesis is provided for repairing a fistula. The prosthesis or fistula repair device may include a body with a shape configured for placement in the fistula. The prosthesis may also include an anchor or base that is located at one or both ends of the body to facilitate anchoring the prosthesis in position.

The prosthesis may be configured to allow tissue ingrowth, revascularization and/or neovascularization for repairing the fistula. The prosthesis may be configured to allow fluid flow or passage therethrough to permit drainage and/or irrigation of the fistula. The prosthesis may be formed from a biocompatible material that may integrate into surrounding tissue.

The prosthesis may include one or more channels or passages that extend along part or the entire the length of the prosthesis to create one or more pathways for drainage and/or irrigation of the fistula. At least one of the channels may also extend through an anchor or base provided at an end of the body. The prosthesis may also include one or more channels or passages that extend in a direction that is transverse or lateral relative to the length of the prosthesis to create additional pathways for drainage and/or irrigation of the fistula. If desired, one or more of the transverse or lateral channels may be fluidly coupled with one or more of the longitudinal channels to create a network of passages for drainage and/or irrigation. The channels may have any suitable configuration as should be apparent to one of skill in the art. For example, and without limitation, the channels may be straight, angled, curved or multi-directional. The channels may also allow tissue ingrowth, revascularization and/or neovascularization to the prosthesis for completing the fistula repair.

The prosthesis may include a longitudinal channel or passage that has a relatively uniform inner dimension, such as diameter, along its length. Alternatively, and without limitation, the channel or passage may have an inner dimension or diameter that increases in a direction from a first end of the prosthesis toward a second end of the prosthesis. The prosthesis may be positioned within a fistula so that the first end is positioned toward the primary opening of the fistula and the second end is positioned toward the secondary opening of the fistula. This arrangement may permit continued drainage of the fistula as the tapered channel eventually closes over time in a direction from the first end toward the second end.

The prosthesis may include a body having a configuration that approximates a fistula shape. For example, and without limitation, the body may have an elongated cylindrical configuration or an elongated tapered shape. A tapered configuration may employ a body having a size that decreases in a direction from the first end toward the second end of the prosthesis. The body may be sufficiently flexible to allow the prosthesis to bend and/or conform to the contour of the fistula tract which could have a curved or sinuous pathway.

The prosthesis may include stacked layers of biocompatible material. If desired, one or more layers of material may be removed or added to adjust the shape, including the length, of the prosthesis for a particular application.

A layer may be positioned in spaced relation to an adjacent layer. A spaced layer arrangement may provide the prosthesis with one or more channels or passages between the layers that allow one or more of the following: fluid flow therethrough, tissue ingrowth, revascularization and neovascularization. The spaced layer arrangement may provide a desired flexibility that allows the prosthesis to conform to the shape or contour of the fistula tract.

The layers may be arranged to maintain a spacing therebetween. One or more spacers may be located between adjacent layers. Such an arrangement may help reduce the potential of the prosthesis collapsing into a relatively rigid mass of material after implantation.

Each layer may have at least one opening extending therethrough. The openings may form a channel or passage to allow drainage and/or irrigation of the fistula. The openings may also or alternatively facilitate tissue ingrowth, revascularization and/or neovascularization through the prosthesis. The openings may also or alternatively provide the prosthesis with a desired amount of support, compliance and/or flexibility. The openings may have any suitable configuration to provide the prosthesis with one or more of these or other desired characteristics as should be apparent to one of skill in the art.

The layers may have a circular shape to provide the body with an overall shape that may approximate the fistula tract. The edges of the layers may be formed or cut to create or enhance grip along the fistula tract. The layers may be the same size to provide the body with a generally cylindrical configuration. Alternatively, and without limitation, one or more of the layers may have different sizes to provide the body with a tapered or generally frusto-conical configuration. In this manner, the body may be formed with a configuration that approximates the particular shape of the fistula tract.

Each anchor or base layer may have a dimension that is larger than the outer periphery of the body and the primary and secondary openings of the fistula to help anchor the prosthesis in position. In this regard, each anchor or base may be fastened to tissue adjacent the fistula openings using, for example, sutures, staples or other suitable fasteners.

The prosthesis may be configured with an adjustable length for accommodating fistula tracts of varying lengths. The body may include a first body portion and a second body portion that are adjustable relative to each other to increase or decrease the overall length of the prosthesis. A first anchor may be provided at a first end of the first body portion and second anchor may be provided at a second end of the second body portion. In one embodiment, the prosthesis may employ a telescopic arrangement in which one body portion is slidably received within the other body portion to adjust the overall length.

The prosthesis may employ a body that includes a plurality of elongated body segments that are configured to extend along the fistula tract. Each body segment may have a cord-like configuration that provides the body with a fringe-like appearance. The body segments may provide a wicking or capillary function to facilitate drainage of the fistula tract. An anchor or base may be provided at one end of the body to anchor and maintain the prosthesis in position within the fistula tract. The anchor may be provided with one or more openings for drainage and/or irrigation.

The elongated body segments may be arranged in a generally cylindrical or tubular pattern that provides a central channel or passage for drainage and/or irrigation of the fistula. Aspects of one end of the body segments may be organized to help maintain the shape of the body. The opposite ends of the body segments may remain loose or free of attachment to each other so that they can move and/or be manipulated independent of one another. Alternatively, and without limitation, aspects of both ends of the elongated body segments may be organized to help keep the body segments in position relative to each other.

The prosthesis may include a support and/or containment structure for supporting and/or containing the elongated body segments. Such an arrangement may facilitate placement of the prosthesis within a fistula tract. The support structure may include a length of material that is wrapped in a spiral pattern about and along at least a portion of the length of the body to support and/or contain the body segments. Alternatively, and without limitation, the support structure may include one or more bands of material that are wrapped about select regions of the body. If desired, the support structure may include one or more bands or discs of material with the body segments extending through each band. The bands may be spaced at select regions along the length of the body. Each band or disc may include an opening to form a channel or passage that extends along the length of the prosthesis.

The prosthesis may employ a body that includes a plurality of elongated body segments that are braided together. Such an arrangement may facilitate placement of the prosthesis within a fistula tract. The body segments may be maintained in a braided configuration using one of more bands or discs of material that are located at select regions along the length of the braid.

The prosthesis may include one or more tethers, such as sutures, that extend from one or each end of the prosthesis to facilitate insertion into the fistula and/or positioning of the prosthesis relative to the fistula. At least one tether may have sufficient length to extend along the fistula and out of the first and/or secondary opening so that the tether may be manipulated from outside a patient's body to pull the prosthesis along and position it within the fistula tract. The tethers may also be manipulated to position one or both ends of the prosthesis at the primary and/or secondary openings.

The prosthesis may be formed from a biocompatible material that may integrate into surrounding tissue. The prosthesis may be formed from a biologic and/or synthetic material. The biologic material may or may not be cross-linked to provide the prosthesis with any desired amount of strength, flexibility and/or absorbability for one or more particular applications. For some applications, the prosthesis may include biologic materials having varying degrees of crosslinking to vary the strength, flexibility, absorbability and/or other property of one or more select portions of the prosthesis. For some applications, the prosthesis may include a combination of biologic and synthetic materials.

For ease of understanding, embodiments of the implantable prosthesis will be described below in connection with an anal fistula repair. However, it is to be understood that aspects of the invention may be employed for a prosthesis having any shape suitable for repairing other types of fistulas as should be apparent to one of skill in the art.

As illustrated in FIG. 1, an anal fistula 30 may form between the anal canal 32, including the colon, bowel or rectum, and the perianal skin 34. A fistula tract 36 may extend from a primary opening 38 within the anal canal to a secondary opening 40 through the perianal skin. Although illustrated as relatively straight, it is to be appreciated that the fistula tract 36 may have a curved or sinuous pathway, or other shape.

Figure 2:
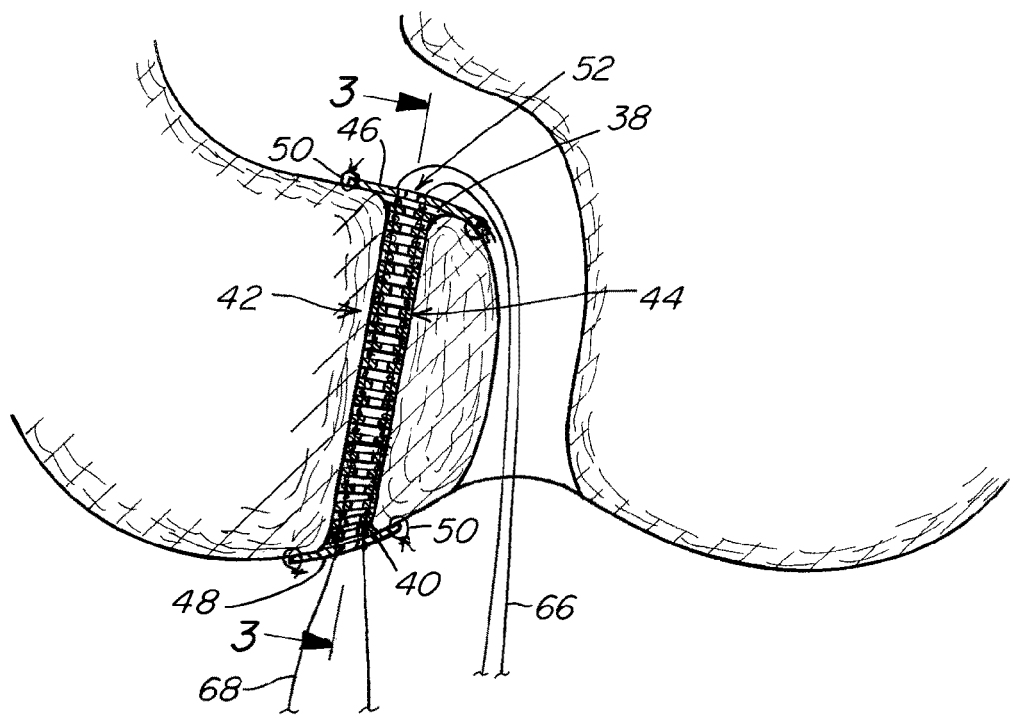
FIG. 2 illustrates the anal fistula of FIG. 1 being repaired with an implantable fistula repair device according to one embodiment of the invention.

In one illustrative embodiment as shown in FIG. 2, an implantable prosthesis 42 may be placed within the fistula tract. The prosthesis may promote healing of the fistula. The prosthesis may also facilitate drainage and/or irrigation of the fistula.

Prior to installing the prosthesis, the fistula may be cleaned of contaminants using any suitable procedure as should be apparent to one of skill in the art. For example, and without limitation, the fistula may be cleaned by debriding the fistula while providing irrigation and suction to remove loosened contamination.

In one illustrative embodiment, the prosthesis 42 may include a body 44 that is configured to extend along the fistula tract. As shown in FIG. 2, the body 44 may extend along the entire length of the fistula tract. However, if desired, the prosthesis may extend along only a portion of the fistula tract.

The prosthesis 42 may include an anchor or base that is located at one or both ends of the body to facilitate anchoring the prosthesis in position. As shown in FIG. 2, the prosthesis may include an anchor at each end of the body. A first anchor 46 may be used to anchor a first end of the body at the primary opening 38 of the fistula and a second anchor 48 may be used to anchor a second end of the body at the secondary opening 40 of the fistula. However, it is to be appreciated that an anchor is not required at each end of the body. For example, and without limitation, the prosthesis may include an anchor only at the first end of the body to anchor the prosthesis at the primary opening.

The prosthesis may be secured to muscle, tissue and/or skin adjacent the primary and/or secondary opening using one or more sutures 50 that secure the anchors in position. However, the prosthesis may be secured to muscle, tissue and/or skin, as desired, using any suitable technique as should be apparent to one of skill in the art.

The prosthesis may include one or more channels or passages that extend along part or the entire length of the prosthesis to create one or more pathways for drainage and/or irrigation of the fistula. In one illustrative embodiment shown in FIGS. 2-4, the prosthesis 42 may include a central channel 52 that extends through the body. As shown, the channel may also extend through each anchor or base 46, 48 provided at the ends of the body. However, if desired, the channel may not extend through the first anchor or base 46 to block potential contamination from entering the fistula from the anal canal.

In one illustrative embodiment, the prosthesis 42 may include one or more channels or passages 54 that extend in a direction that is transverse or lateral relative to the length of the prosthesis to create additional pathways for drainage and/or irrigation of the fistula. The channels or passages may be angled, whether acute, obtuse or normal, relative to the length of the prosthesis. The channels or passages may also allow tissue ingrowth, revascularization and/or neovascularization to the prosthesis for completing the fistula repair.

Figure 3:
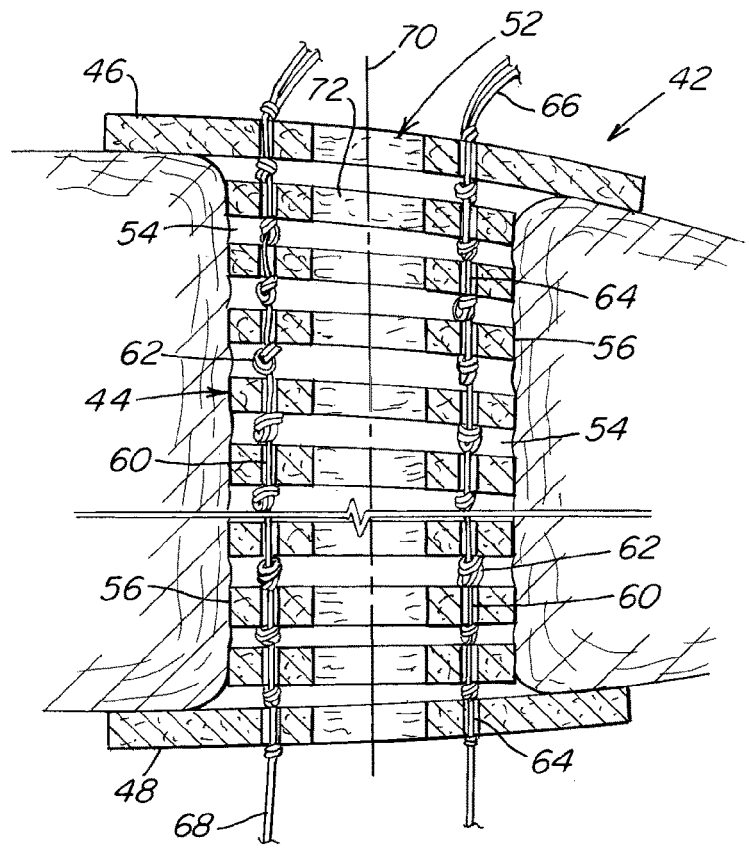
FIG. 3 is a cross-sectional view of the fistula repair device of FIG. 2 taken along section line 3-3.
Figure 4:
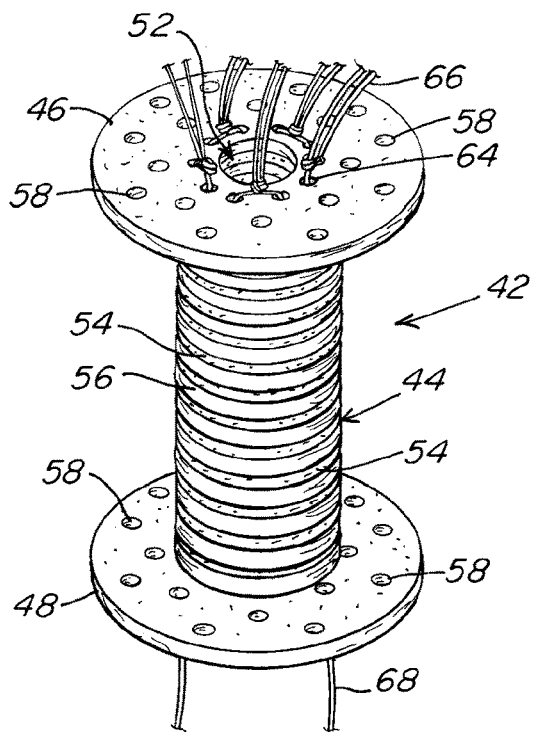
FIG. 4 is a perspective view of the fistula repair device of FIGS. 2-3.
Figure 5:
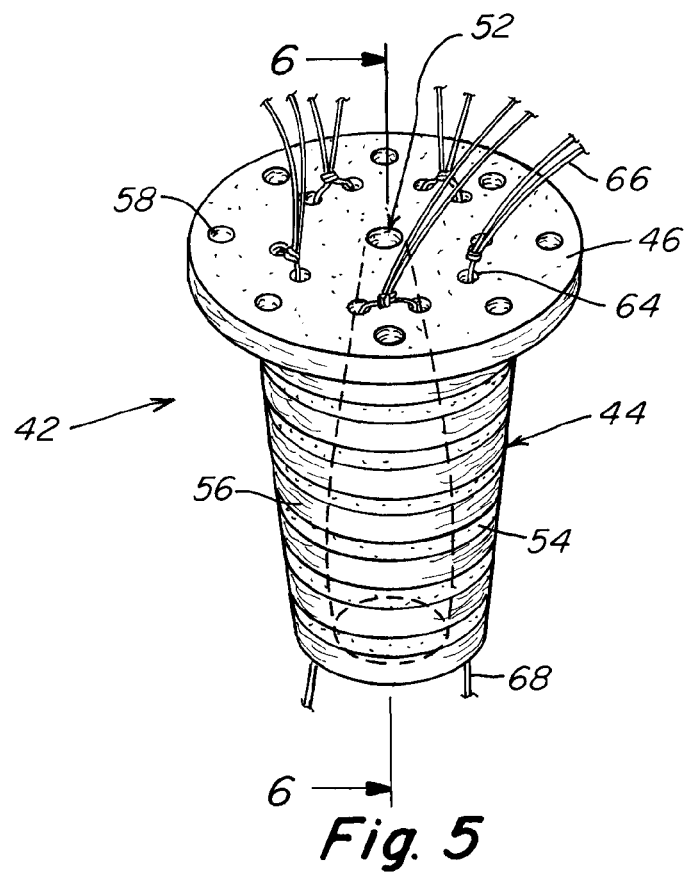
FIG. 5 is a perspective view of an implantable fistula repair device according to another embodiment of the invention.

In one illustrative embodiment shown in FIGS. 2-4, the body 44 may include a plurality of layers 56 of biocompatible material arranged in a stacked configuration. As shown, each layer 56 may be positioned in spaced relation to an adjacent layer to provide the prosthesis with channels 54 between the layers for fluid flow, tissue ingrowth, revascularization and/or neovascularization. The spaced layers 56 may also provide the prosthesis with a desired amount of flexibility to allow the prosthesis to bend and conform to the contours of the fistula.

Each anchor 46, 48 may include one or more layers of biocompatible material located at an end of the body. The number and particular configuration of the anchor layers may depend on the particular characteristics desired for the anchor.

In one embodiment, each anchor or base layer 46, 48 may include one or more holes 58 for securing the base with a fastener, such as a suture. The anchor holes 58 may be located in the outer or peripheral portion of the anchor layers that extends beyond the body to facilitate securement of each anchor. The peripheral holes may also permit tissue ingrowth to the base over time to more permanently anchor the prosthesis in position. As shown, the anchor layer may provide a relatively large surface area for securing and/or anchoring the prosthesis.

The layers, including the body layers 56 and the anchor layers 46, 48, may be secured or fixed in position to maintain the spacing therebetween and maintaining the shape of the prosthesis. Such an arrangement may help reduce the potential of the layers collapsing upon each other and transforming the prosthesis into a relatively rigid mass of material after implantation. This arrangement may also maintain a desired level of flexibility or bendability for the prosthesis.

In one illustrative embodiment shown in FIGS. 3-4, the layers 56 may be secured together using one or more lengths of suture 60 or suture-like material. As illustrated in FIG. 3, the spacing between adjacent layers 46, 48, 56 may be maintained by forming one or more knots 62 in the suture between each of the layers. The particular spacing between adjacent layers may be established by the number and/or size of knots formed between the layers. It is to be understood that other arrangements for spacing apart and maintaining adjacent layers in spaced relation may be employed as should be apparent to one of skill in the art. For example, and without limitation, one or more spacers may be integrally formed in a layer. Alternatively, one or more standoffs may be provided between adjacent layers.

In one embodiment, the spacing between each layer of the stack may be uniform. For example, the layers 46, 48, 56 may be uniformly spaced by providing similar knots 62 between adjacent layers. In another embodiment, the spacing may be varied between some or all of the layers. For example, and without limitation, the size and/or number of knots 62 between some layers may be smaller or larger than the size and/or number of knots between other layers.

One illustrative embodiment of a method of fabricating or assembling a prosthesis with a stacked configuration is described in connection with FIGS. 3-4.

As shown in FIG. 3, several lengths of suture 60 may be extended or threaded through holes or openings 64 provided in the second anchor or base layer 48 of the prosthesis. Each suture 60 is tied to form one or more knots 62 to create a desired amount of spacing between the next layer of material. Once knotted, the lengths of suture 60 are then threaded through another layer of material and again knotted. Additional layers may be added and secured in a similar manner until the desired number of layers are stacked and secured to form the prosthesis, such as shown in FIGS. 3-4.

As shown in FIGS. 3-4, the first anchor or base layer 46 may be secured to the body stack in a similar manner. Once knotted, one or more lengths of the suture material 60 may extend away from the first anchor layer to form one or more tethers 66 to facilitate installation and/or placement of the prosthesis. If desired, additional suture material may extend away from the second anchor layer 48 to form one or more tethers 68 to facilitate installation and/or placement of the prosthesis.

The suture material extending from one or both ends of the prosthesis may have sufficient length to facilitate implanting and positioning the prosthesis in the fistula. In one embodiment, the sutures or tethers 66, 68 may be pulled through the fistula from either the primary opening 38 or the secondary opening 40 to thereby pull the prosthesis into and along the fistula tract. The sutures may also be manipulated to help position one or both anchors 46, 48 at the respective opening. Once the prosthesis is implanted in the fistula, the sutures or tethers may be cut off or left in place to facilitate repositioning or removal of the prosthesis, if necessary.

As described above, assembly of the prosthesis may be initiated with the second anchor layer and built up toward the first anchor layer. However, it is to be appreciated that the prosthesis may be assembled in the reverse manner from the first anchor layer to the second anchor layer, if desired, with one or more lengths of the suture material extending away from the second anchor layer.

As indicated above, it may be desirable to construct the prosthesis with one or more channels or passages that allow drainage and/or irrigation of the fistula. The channel may be a continuous passage that extends through a portion of the prosthesis, or the channel may be formed by one or more openings that extend through individual layers and together create the channel or passage when stacked together.

In one illustrative embodiment shown in FIGS. 3-4, the prosthesis 42 may include a channel 52 or passage that extends along the entire length of the body 44 and the anchors 46, 48. As shown, the channel may be centrally located along the longitudinal axis 70 of the prosthesis. The channel 52 may be formed by at least one opening 72 extending through each layer 46, 48, 56 of the prosthesis which align when the layers are stacked and secured together to form the prosthesis.

For some applications, the channel may be offset from the longitudinal axis and/or located in other regions of the prosthesis. The channel may extend along a portion or the entire length of the prosthesis. If desired, the channel may be angled relative to the longitudinal axis, curved and/or extend in multiple directions to provide a desired pathway through the prosthesis.

The longitudinal channel 52 may communicate with one or more transverse or lateral channels or passages 54 located between adjacent layers to allow drainage and/or irrigation through the prosthesis in both the axial and lateral directions. The channel may also permit for tissue ingrowth, revascularization and/or neovascularization to the prosthesis.

As illustrated in FIGS. 3-4, each layer may also include holes or openings 64 for securing the layers together with a suture, as described above. If desired, these holes may be configured to form additional channels or passages through the prosthesis for drainage, irrigation, tissue ingrowth, revascularization and/or neovascularization.

The number, configuration and pattern of the holes or openings 64 may be selected to provide any desired characteristics as should be apparent to one of skill in the art. For example, in addition to drainage, tissue ingrowth and/or vascularization characteristics, the compliance, resiliency or flexibility of the prosthesis may be changed by varying the number, size, shape and/or pattern of holes or openings provided in one or more of the layers of material.

In the illustrative embodiments of FIGS. 3-4, some or all of the layers of the prosthesis may include a first hole or opening 72 that is centrally located to form a channel 52 along the longitudinal axis 70 of the prosthesis. Some or all of the layers may also include a group of second holes 64 arranged about the first hole. As described above, the second holes 64 may be used for securing the layers together with suture. The second holes may also form additional channels or passages through the prosthesis.

In the embodiments described above, the applicable layers may employ a uniform pattern of holes or openings 64, 72 that align with each other when the layers are assembled in the stacked configuration. The anchor layers may have additional peripheral holes 58 for securing the prosthesis in position during the repair procedure. However, it is to be understood that two or more of the layers may include holes or openings having different sizes, shapes and/or patterns as should be apparent to one of skill in the art.

The body 44 and the anchors or bases 46, 48 of the prosthesis may employ any shape suitable for a particular application. As illustrated in the embodiment of FIGS. 3-4, the prosthesis may include a body 44 having a generally cylindrical shape with a size suitable for repairing a particular fistula. The prosthesis may include one or more anchors 46, 48 having a circular shape with a diameter that is larger than the body and the fistula tract to facilitate anchoring of the prosthesis.

The length of the body may be increased or decreased by adding or removing layers. In this regard, the length of the body may be decreased by severing the suture between one or more of the layers that are to be removed from the body. This arrangement allows a surgeon to quickly adjust the length of the prosthesis during a fistula repair procedure.

In one illustrative embodiment shown in FIGS. 5-8, the fistula repair device 42 may include a body 44 having a tapered or frusto-conical shape that may be suitable for repairing a fistula having a similarly tapered shape. The body 44 may be formed with layers 56 of material having outer dimensions, such as diameters, that decrease in a direction from one end of the body toward the opposite end of the body. As shown, the body 44 may taper from the first anchor 46 toward the opposite end of the body. If desired, a second anchor may be provided at the second end of the tapered body.

Figure 6:
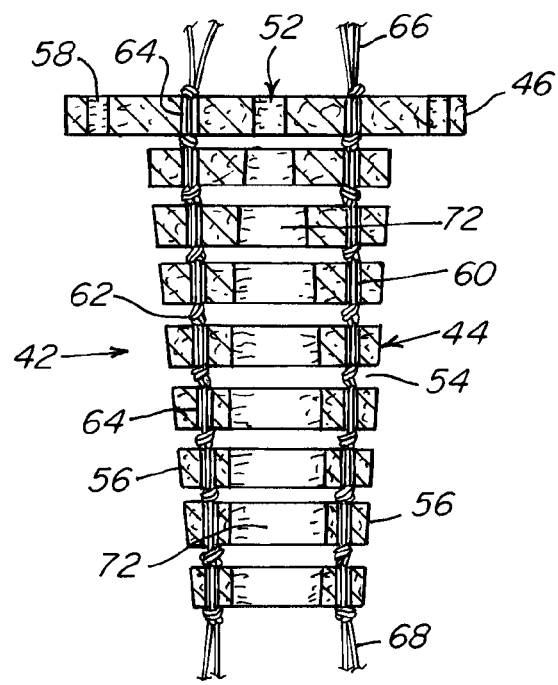
FIG. 6 is a cross-sectional view of the fistula repair device of FIG. 5 taken along section line 6-6.
Figure 7:
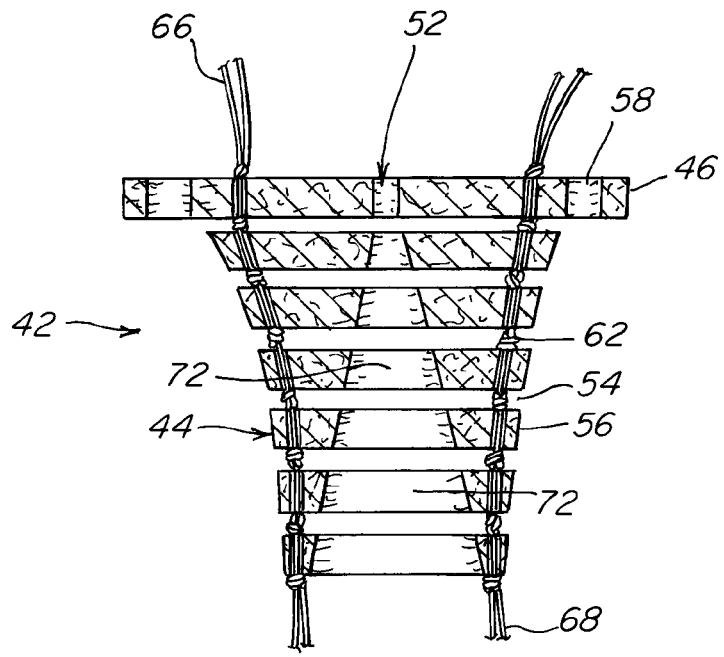
FIG. 7 is a cross-sectional view of an implantable fistula repair device according to another embodiment of the invention.

For some applications, it may be desirable to provide a channel or passage having a configuration and/or size that varies along its length to facilitate fistula repair while allowing drainage from the fistula. In one illustrative embodiment shown in FIGS. 6-7, the channel 52 may have an inner dimension, such as a diameter, that increases along at least a portion of its length in a direction from the first end of the body toward the second end of the body. As shown in FIG. 6, the channel 52 may increase in size along a selected portion of its length. As shown in FIG. 7, the channel 52 may increase in size along its entire length. Such configurations may promote healing of the fistula in a direction from the primary opening toward the secondary opening while maintaining drainage of the fistula from the secondary opening as the fistula heals and closes up in a direction from the primary opening toward the secondary opening.

Figure 8:
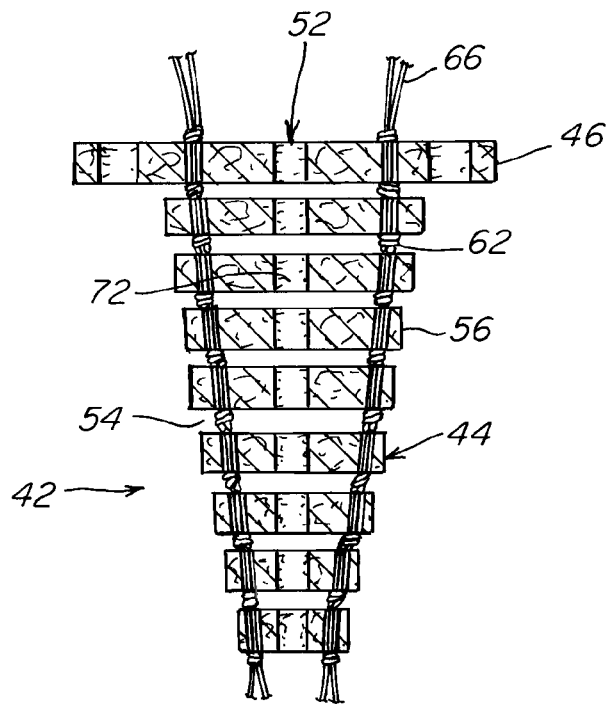
FIG. 8 is a cross-sectional view of an implantable fistula repair device according to another embodiment of the invention.

If desired, the fistula repair device 42 may employ a channel having a constant or uniform diameter along the length of the body. In one illustrative embodiment shown in FIGS. 3 and 8, the fistula repair device may employ a drainage channel 52 or passage having a uniform diameter along its length. As shown in FIG. 3, the prosthesis may include a body 44 with a uniform outer diameter and an internal channel 52 with a uniform diameter. As shown in FIG. 8, the prosthesis may include a body 44 with a tapered outer diameter and an internal channel 52 with a uniform diameter.

Although several embodiments of a fistula repair device have been described with various body and channel configurations, it is to be understood that the fistula repair device may employ any combination of body and channel shape or configurations as should be apparent to one of skill in the art.

In one illustrative embodiment, a fistula repair device 42 may be formed with stacked layers 46, 48, 56 having a thickness of approximately 0.04 to 0.08 inches (1 to 2 mm) that are spaced apart to form a gap or opening of approximately 0.08 to 0.12 inches (2 to 3 mm). Each body layer 56 may have a diameter of approximately 0.20 to 0.80 inches (5 to 20 mm) and each anchor or base layer 46, 48 may have a diameter of approximately 0.40 to 2.4 inches (10 to 60 mm). Each layer may have a hole or opening 72 having a diameter of approximately 0.08 to 0.32 inches (2 to 8 mm) to form the drainage channel or passage. For a tapered configuration, the body 44 may have an outer diameter that tapers from approximately 0.40 to 0.80 inches (10 to 20 mm) at the first end to approximately 0.20 to 0.40 inches (5 to 10 mm) at the second end. The body 44 may have a drainage channel 52 with a diameter that tapers from approximately 0.08 to 0.16 inches (2 to 4 mm) at the first end to approximately 0.16 to 0.32 inches (4 to 8 mm) at the second end. The prosthesis may have a length of approximately 2.4 to 4.0 inches (6 to 10 cm). It is to be understood that the prosthesis may be configured with features having any suitable size and/or shape as should apparent to one of skill for any particular application.

The various embodiments described above employ a stacked layer arrangement for the prosthesis. However, it is to be understood that the fistula repair device may employ other structural arrangements of materials to provide the prosthesis with any suitable combination of desired features and/or characteristics. Several non-limiting embodiments of other fistula repair devices are described below.

Figure 9:
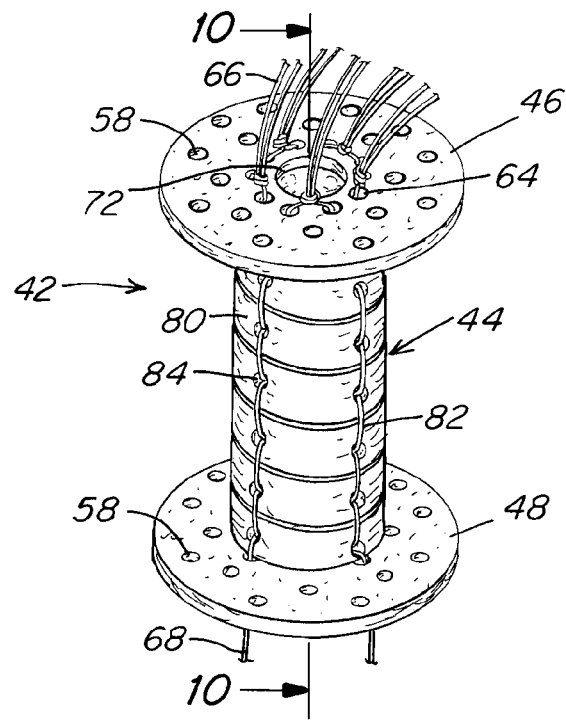
FIG. 9 is a perspective view of an implantable fistula repair device according to another embodiment of the invention.
Figure 10:
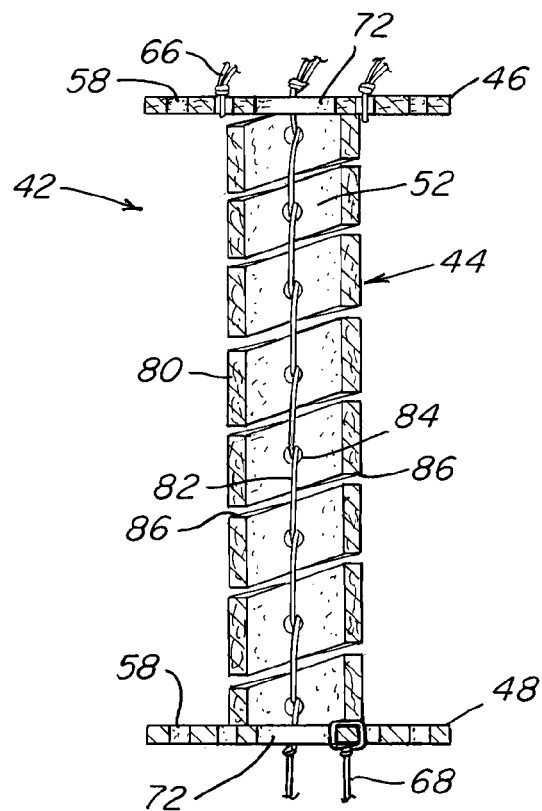
FIG. 10 is a cross-sectional view of the fistula repair device of FIG. 9 taken along section line 10-10.

In one illustrative embodiment shown in FIGS. 9-10, the fistula repair device 42 may include a body 44 with first and second anchors 46, 48 located at opposite ends of the body with a diameter that is larger than the body. The body 44 may include a sidewall 80 that extends from the first anchor 46 to the second anchor 48. The body 44 defines a channel 52 or passage for drainage and/or irrigation of the fistula. The anchors may each have at least one opening or hole 72 in communication with the channel.

As illustrated, the body 44 may have a cylindrical or tubular shape that conforms to a fistula tract. Such an arrangement may be desirable to provide a prosthesis having relatively less material and bulk. However, the body may be configured to have any shape suitable for repairing a fistula as should be apparent to one of skill in the art. For example, and without limitation, other body shapes may include tapered, conical and frusto-conical shapes.

In one illustrative embodiment, the body may be formed from a length or strip of biocompatible material that is wrapped into the desired shape. In one embodiment, the sidewall 80 may be formed by wrapping the material in a helix or spiral pattern. Such an arrangement may be desirable to increase the relative flexibility of the body. However, it is to be understood that the sidewall may be formed by wrapping the material in any suitable pattern as should be apparent to one of skill in the art.

The body material may be retained in the desired shape using one or more fasteners. In one embodiment, the sidewall 80 may be formed by securing or retaining the material in the desired shape with one or more lengths of suture 82 or suture-like material. As illustrated, the suture may extend in a vertical direction and be anchored in holes 84 that are aligned when the material is placed in the desired shape. One or more knots may be formed in the suture and located on the inner side of the material to retain the suture in the hole. It is to be understood that any suitable fastener or fastening scheme may be used to retain the body material in the desired shape. For example, and without limitation, the edges of the wrapped material may be adhered or bonded together using a suitable adhesive for the particular material as should be apparent to one of skill.

In one embodiment, the material may be wrapped to position adjacent edges 86 of the wrapped material in close proximity to each other so that there is a minimal, if any, gap between the edges. However, the sidewall 80 may be configured with adjacent edges of material being spaced apart to form an opening therebetween that may allow drainage, tissue ingrowth, revascularization and/or neovascularization through the sidewall of the body.

The anchors or bases 46, 48 may be secured to the opposing ends of the body 44 using one or more fasteners. In one embodiment, the anchors 46, 48 may be secured to the body sidewall 80 using the sutures 82 that also retain the sidewall material in the desired shape. If desired, separate fasteners may be used to secure the anchors to the sidewall.

Figure 11:
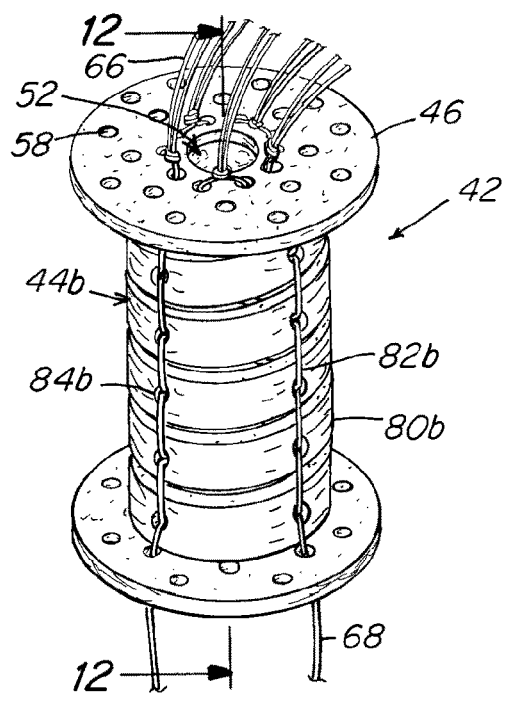
FIG. 11 is a perspective view of an implantable fistula repair device according to another embodiment of the invention.

For some applications, it may be desirable to adjust the length of the prosthesis to accommodate fistula tracts of varying lengths. In one illustrative embodiment shown in FIGS. 11-12, the body 44 may include a first body portion 44a and a second body portion 44b that are adjustable relative to each other to increase or decrease the overall length of the prosthesis. As shown, a first anchor 46 may be provided at a first end of the first body portion 44a and second anchor 48 may be provided at a second end of the second body portion 44b.

Figure 12:
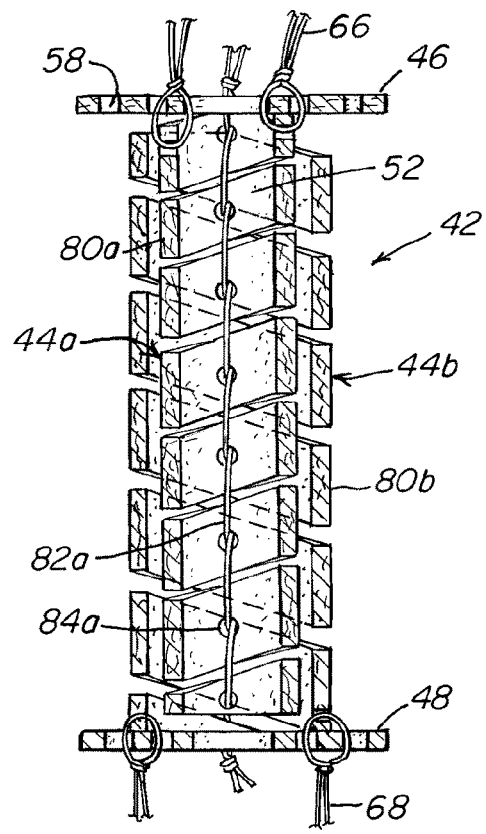
FIG. 12 is a cross-sectional view of the fistula repair device of FIG. 11 taken along section line 12-12.

In one illustrative embodiment shown in FIG. 12, the prosthesis 42 may employ a telescopic arrangement for adjusting its overall length. As illustrated, the first body portion 44a may be slidably received within the second body portion 44b. The first and second body portions 44a, 44b may have tubular configurations with the first body portion 44a being smaller than the second body portion 44b.

In one illustrative embodiment, each of the first and second body portions 44a, 44b may be formed from a length or strip of biocompatible material that is wrapped into the desired shape. In one embodiment, each body portion 44a, 44b may include a sidewall 80a, 80b that is formed by wrapping the material in a helix or spiral pattern. As shown, the body portions may employ helix patterns that are wound in opposite directions relative to each other. However, it is to be understood that the body portions may be formed by wrapping the material in any suitable pattern as should be apparent to one of skill in the art.

The material for each body portion may be retained in the desired shape using one or more fasteners. In one embodiment, the body portions 44a, 44b may be formed by securing or retaining the material in the desired shape with one or more lengths of suture 82a, 82b or suture-like material. As illustrated, the suture may extend in a vertical direction and be anchored in holes 84a, 84b that are aligned when the material is placed in the desired shape, such as described above.

Figure 13:
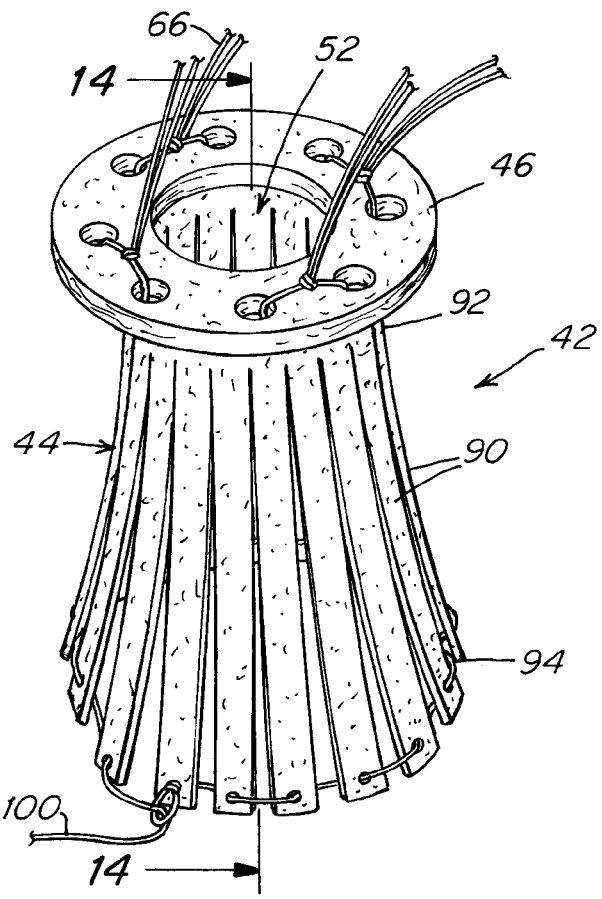
FIG. 13 is a perspective view of an implantable fistula repair device according to another embodiment of the invention.

For some applications, it may be desirable to enhance or facilitate drainage of contaminants from the fistula tract. In one illustrative embodiment shown in FIGS. 13-14, the prosthesis 42 may employ a body 44 that includes a plurality of elongated body segments 90 that are configured to extend along the fistula tract. Each body segment 90 may have a cord-like configuration to provide the body with a fringe-like appearance. The body or fringe segments 90 may provide a wicking or capillary action to facilitate drainage of contaminants from the fistula tract. An anchor or base 46 may be provided at one end of the body for anchoring and maintaining the prosthesis in position within the fistula tract.

The elongated body segments 90 may be arranged in a generally cylindrical or tubular pattern that provides a central channel 52 or passage for drainage and/or irrigation of the fistula. The body or fringe segments 90 may be spaced from each other to provide additional channels along which contaminants may travel to exit the fistula.

When subjected to a radial compressive force, which may occur from compression of buttock muscles, the fringe segments 90 may collapse inwardly upon themselves. When such a compressive force is reduced or ceases, the fringe segments may then return to their uncompressed positions. Such an arrangement may provide a desirable level of comfort to a patient for some applications.

As shown, a first end 92 of each fringe or body segment may be organized to help maintain the shape of the body and facilitate attachment of the body to the anchor. The opposite ends 94 of the fringe or body segments may remain loose so that they can move and/or be manipulated independent of one another.

Figure 15:
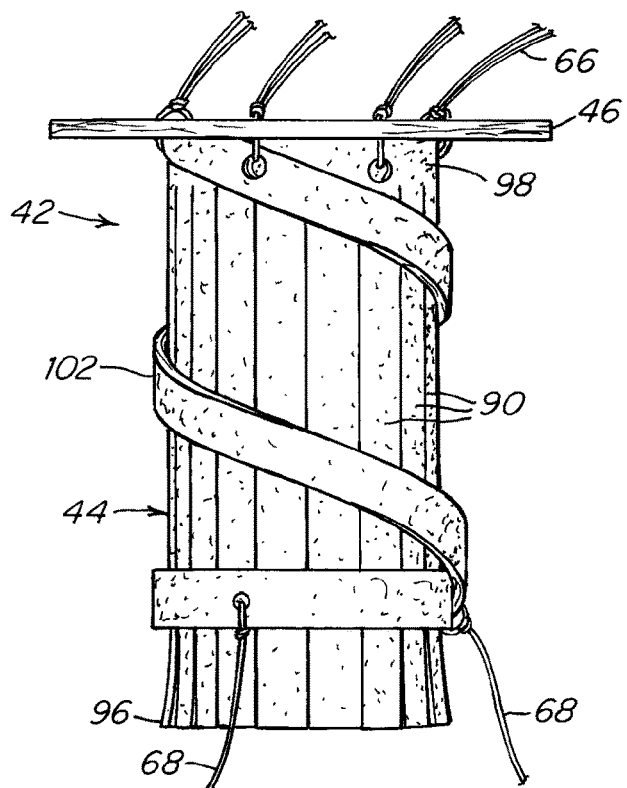
FIG. 15 is a side view of an implantable fistula repair device according to another embodiment of the invention.

In one embodiment as shown in FIG. 15, the body 44 may be formed from a sheet of material that is cut or sliced through one edge 96 and toward a margin 98 located along the opposite edge. The number and spacing of the individual cuts may be selected to form the individual body or fringe segments 90 with channels therebetween along which contamination may travel out of the fistula. When formed into a desirable shape for the body, the margin 98 provides a band of material that may be used to attach the body to the anchor or base. However, it is to be understood that the elongated body segments may be formed and attached to the anchor using any suitable technique as should be apparent to one of skill in the art. For example, and without limitation, each elongated body segment may be a separate component that is individually attached to the anchor.

The prosthesis 42 may be implanted in a fistula by cinching the tails or free ends 94 of the elongated body segments 90 with a tether 100 (FIGS. 13-14), such as a suture, that is pulled through the fistula tract 36. In one embodiment, the repair device 42 may be inserted via the anal canal 32 (FIG. 1) and pulled into and along the fistula tract 36 through the primary opening 38 and toward the secondary opening 40 of the fistula. Once positioned within the fistula tract, the tether 100 may be loosened or removed to free the ends 94 of the body segments 90.

Figure 14:
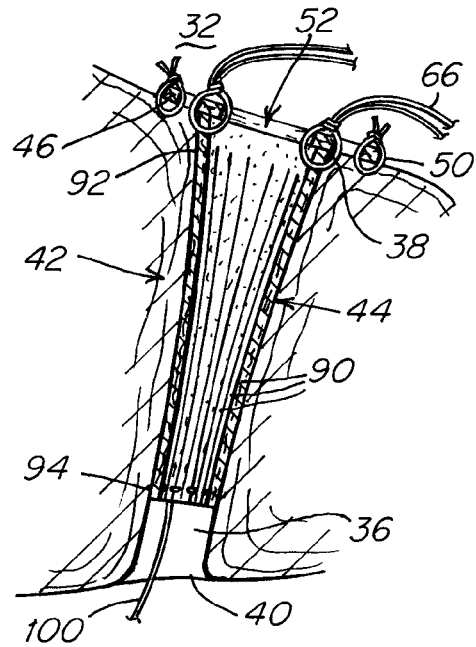
FIG. 14 is a cross-sectional view of the fistula repair device of FIG. 13 taken along section line 14-14 and illustrated being positioned in a fistula.

As shown in FIG. 14, the prosthesis 42 may have a length that is less than the fistula tract so that the tails or free ends 94 of the body or fringe segments 90 remain within the fistula tract. However, it is to be understood that the body may have any suitable length as should be apparent to one of skill in the art. For example, and without limitation, the body segments may have a length that is sufficient to extend outside the fistula tract.

For some applications, it may be desirable to provide the prosthesis with a support and/or containment structure to support and/or contain the fringe segments. Such an arrangement may facilitate implantation of a device with fringe-like segments by maintaining the body in a generally slender configuration.

In one illustrative embodiment shown in FIG. 15, a support structure 102 may include a length of material that is wrapped in a helix or spiral pattern about and along part or the entire length of the body 44 to support and/or contain the body segments 90. The support 102 may be secured to the prosthesis with one or more fasteners, such as sutures, located at select regions of the support. It is to be appreciated that the fistula repair device may employ any suitable support structure, if desired, as should be apparent to one of skill in the art.

Figure 16:
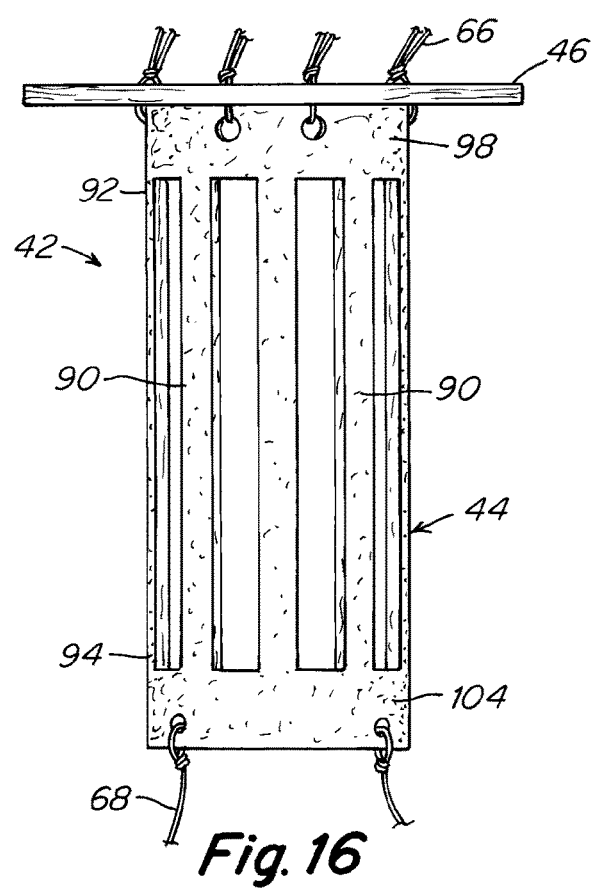
FIG. 16 is a side view of an implantable fistula repair device according to another embodiment of the invention.

In one illustrative embodiment shown in FIG. 16, the prosthesis 42 may employ a body 44 that includes a plurality of elongated body or fringe segments 90 having both ends joined or coupled together to help organize or maintain the body segments in position relative to each other. Such an arrangement may be desirable to facilitate placement of the device within a fistula tract. An anchor or base 46 may be provided at one end of the body for anchoring and maintaining the prosthesis in position within the fistula tract.

In one embodiment, the body 44 may be formed from a sheet of material that is cut or punched to form a plurality of elongated segments 90 that extend between opposing first and second margins of material. When formed into a desirable shape for the body, the first margin 98 of material may be used to attach the body to the anchor or base 46 and the second margin 104 of material retains the second ends 94 of the body segments 90 together to facilitate implantation of the device. After placement of the device within the fistula tract, the second margin 104 may be cut off or otherwise removed, if desired, to provide loose second ends for the fringe segments that may enhance the wicking or capillary action of the device.

Figure 17:
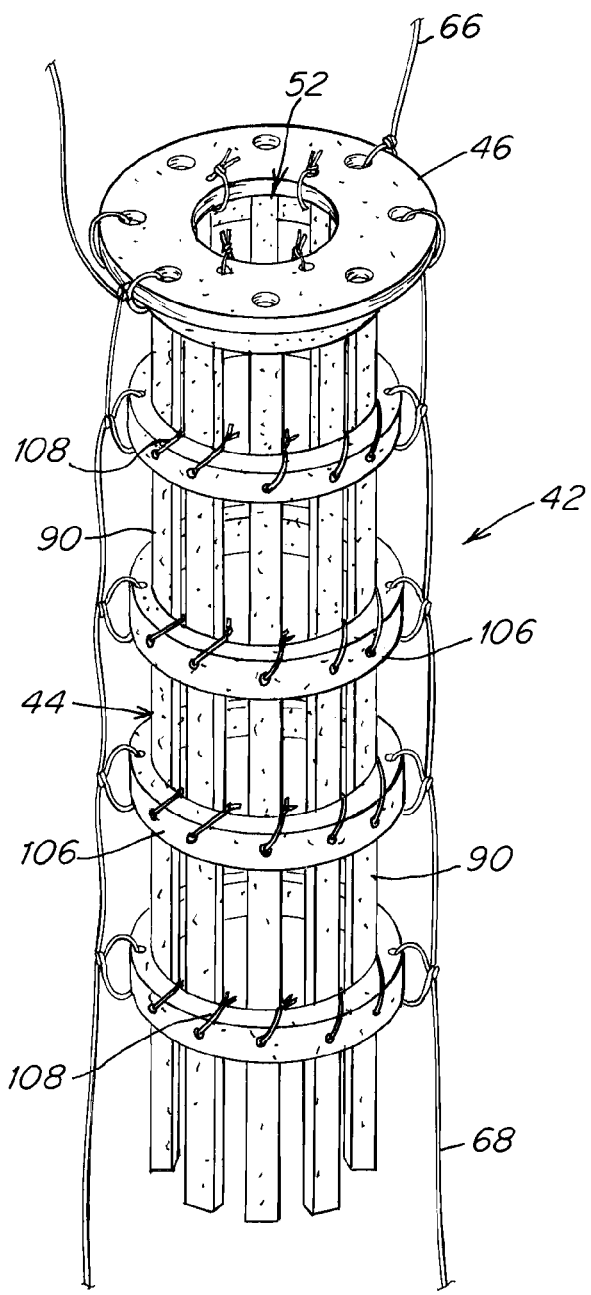
FIG. 17 is a perspective view of an implantable fistula repair device according to another embodiment of the invention.
Figure 18:
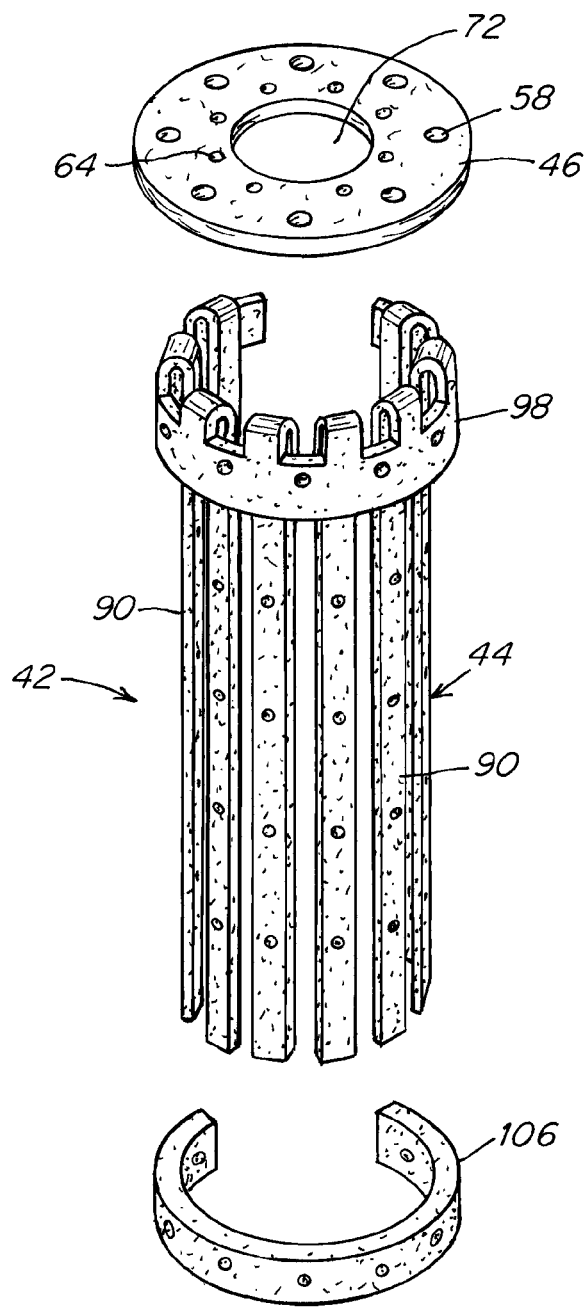
FIG. 18 is an exploded perspective view of the implantable fistula repair device of FIG. 17 illustrating one containment band.

In one illustrative embodiment shown in FIGS. 17-18, the fistula repair device 42 may employ a body 44 that includes a plurality of elongated body or fringe segments 90 with a plurality of support bands or discs 106 located at select regions along the body of the device to help maintain the body segments in position relative to each other. As illustrated, the bands or discs 106 may be secured in position using one or more fasteners 108, such as sutures. An anchor or base 46 may be provided at one end of the body for anchoring and maintaining the prosthesis in position within the fistula tract.

If desired, the body segments may extend through openings (not shown) provided in the annular portion of each disc. The openings may be larger than the body segments to facilitate assembly of the device and provide some free play between the body segments and the discs, if desired.

Figure 19:
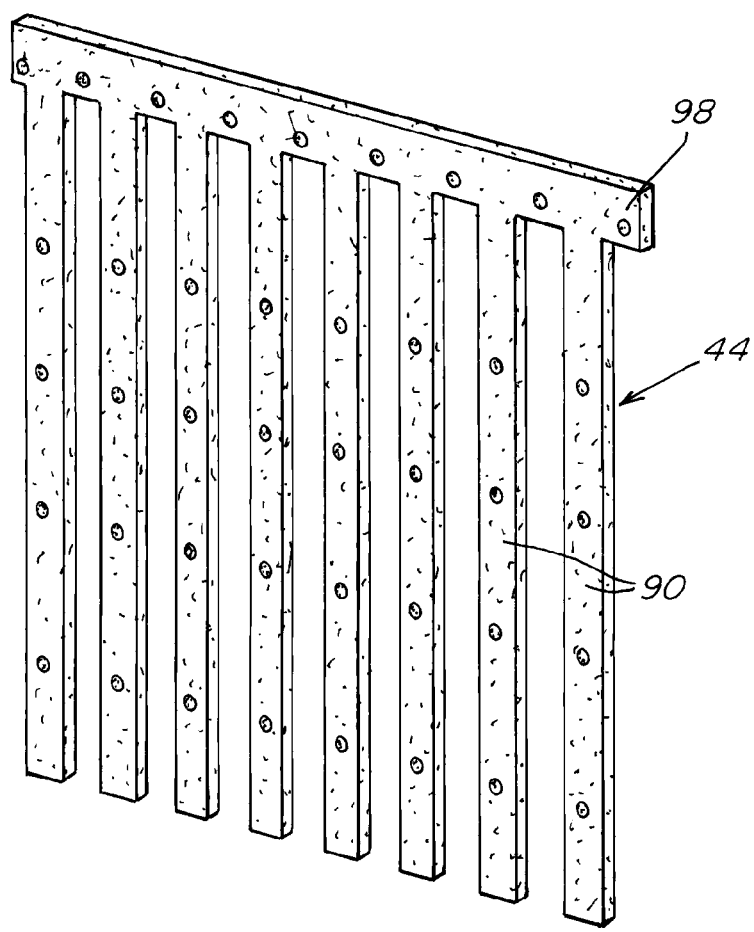
FIG. 19 is a perspective view of a sheet of biocompatible material configured for the body of the implantable fistula repair device of FIGS. 17-18.

In one illustrative embodiment shown in FIG. 19, the body 44 may be formed from a sheet of material that is cut or punched to form the plurality of elongated segments 90 that extend from a margin 98 of material along one edge of the sheet. As shown in FIG. 18, the margin 98 may be folded over to form a band about the body segments 90 that is attached to the anchor 46. Alternatively, the body may be attached to the anchor without folding the margin 98.

For some applications, it may be desirable to provide elongated body segments in a particular arrangement for enhancing the drainage of the fistula tract. In illustrative embodiments shown in FIGS. 20-21, the repair device 42 may employ a body 44 that includes a plurality of elongated body or fringe segments 90 braided together in a desired pattern. The body segments may be maintained in the braided configuration using one of more bands or discs 112 of material that are located at select regions along the length of the braid. The bands or discs 112 may be secured in position using one or more fasteners 114, such as sutures, that attach each band or disc to the braided body. If desired, tethers 66, 68 may be provided to facilitate installation and/or placement of the prosthesis within a fistula tract in a manner similar to that described above.

Figure 20:
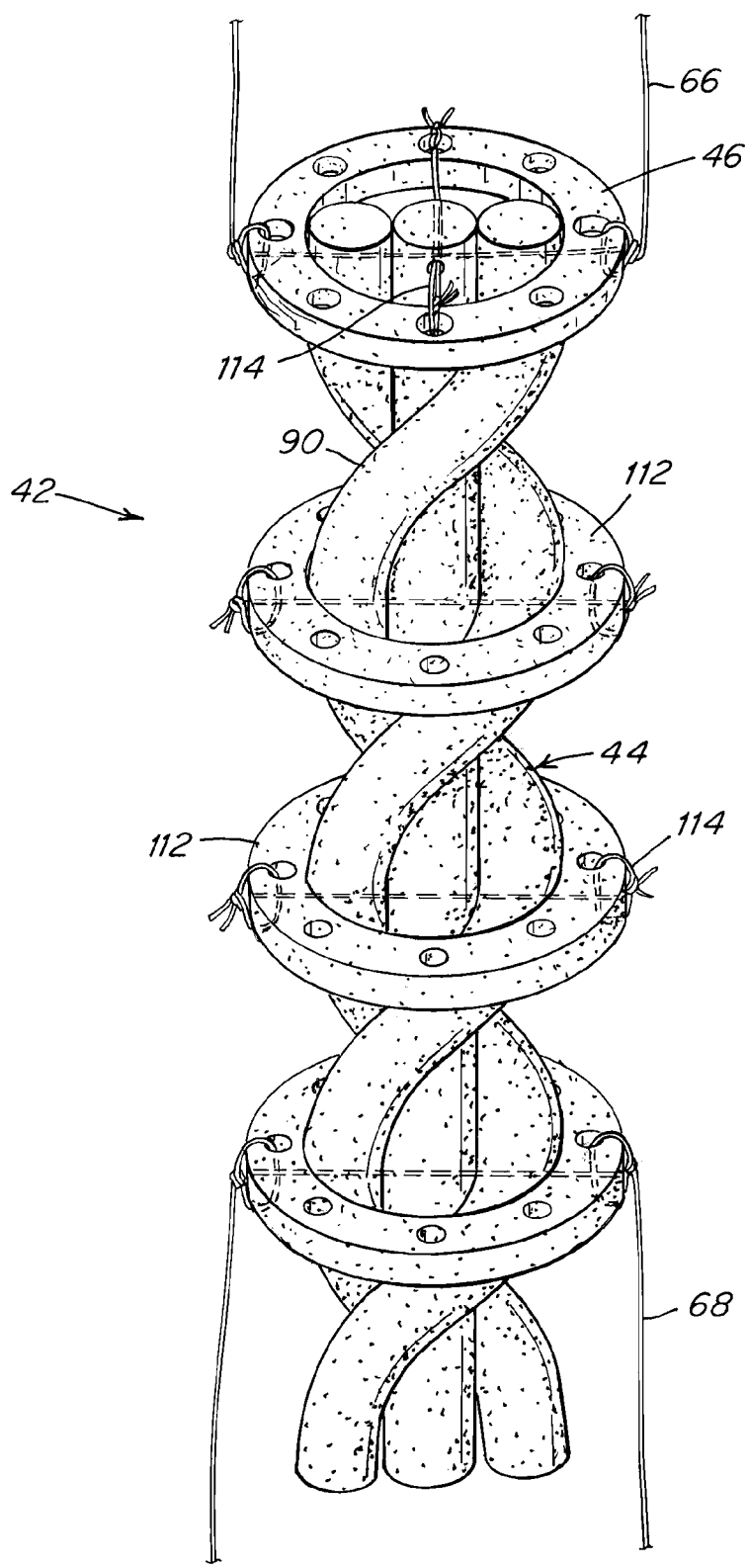
FIG. 20 is a perspective view of an implantable fistula repair device with a braided body according to another embodiment of the invention.
Figure 21:
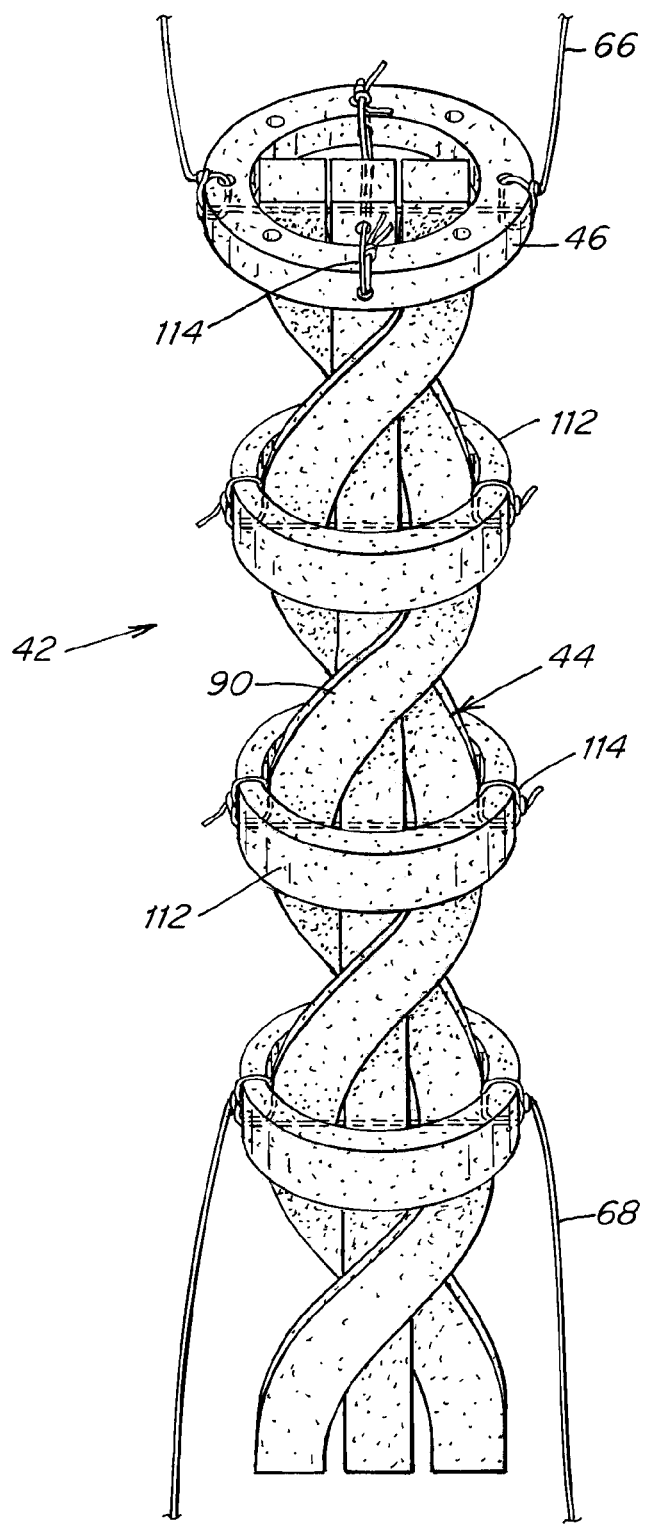
FIG. 21 is a perspective view of an implantable fistula repair device with a braided body according to another embodiment of the invention.

As shown in FIG. 20, each elongated body segment 90 may have a round cross-sectional shape. Alternatively, and without limitation, each elongated body segment 90 may have a rectangular cross-sectional shape, as shown in FIG. 21. However, it is to be understood that each body segment may employ any one or combination of suitable shapes as should be apparent to one of skill in the art. For example, and without limitation, other shapes may include square, triangular, polygonal and oval, and the shapes may be solid or hollow, including tubular shapes.

Figure 22:
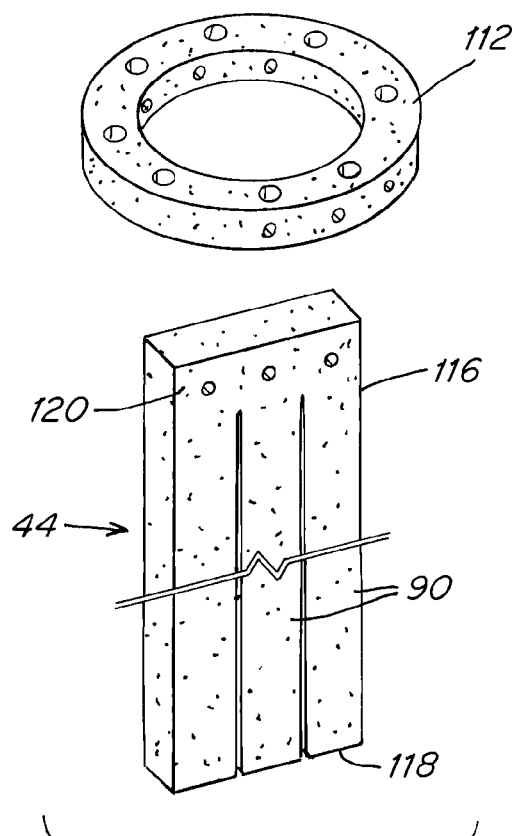
FIG. 22 is an exploded perspective view of an anchor band and a sheet of biocompatible material configured for the body of the implantable fistula repair device of FIG. 21.
Figure 23:
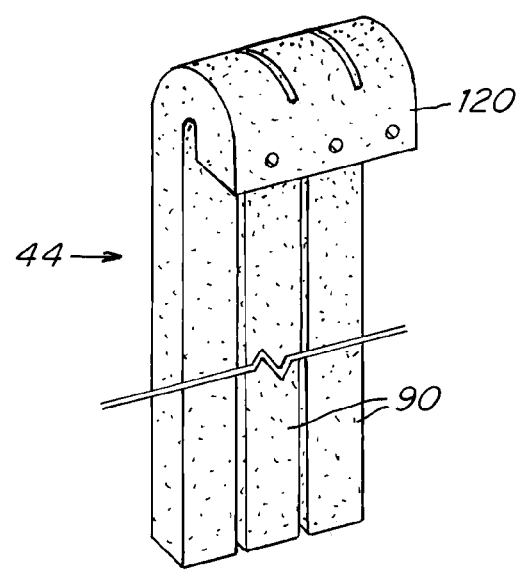
FIG. 23 is a perspective view of the sheet of material of FIG. 22 with a folded margin for attachment to an anchor or base.

In one embodiment as shown in FIGS. 22-23, a body 44 with square body segments 90 may be formed from a sheet of material 116 that is cut or sliced through one edge 118 and toward a margin 120 located along the opposite edge. The number and spacing of the individual cuts may be selected to form the individual body or fringe segments 90. The elongated body segments may be braided together before or after being attached to the anchor 46.

The margin 120 may be used to attach the body 44 to the anchor or base 46. As shown in FIG. 23, the margin 120 may be folded over for attachment to the anchor or base. However, it is to be understood that the elongated body segments may be formed and attached to the anchor using any suitable technique as should be apparent to one of skill in the art. For example, and without limitation, each elongated body segment may be a separate component that is attached to the anchor.

As shown in FIG. 22, each band or disc 112 may be punched or cut from a sheet of material. The band or disc may be formed to have any configuration suitable for supporting the braided body segments in their desired configuration.

The prosthesis may employ any biocompatible material suitable for a particular application as should be apparent to one of skill in the art.

In one embodiment, the prosthesis may be formed from a biologic that may be cross-linked, partially cross-linked or not cross-linked to provide a desired amount of strength, flexibility and/or longevity suitable for the application. The origin of the biologic material may be porcine, bovine or human. Examples of a biologic material that may be suitable for the prosthesis include AlloMax and CollaMend, which are both available from C.R. Bard, Inc. The prosthesis may be hydrated, if desired, prior to implantation.

In other embodiments, the prosthesis may be formed of a synthetic material or a combination of biologic and synthetic materials to provide the prosthesis with desirable properties and/or characteristics as should be apparent to one of skill in the art.

For certain applications or reconstructive procedures, it may be desirable to provide the prosthesis with one or more components for facilitating or enhancing the procedure.

In one embodiment, the prosthetic material may be coated with one or more antibiotic components. Illustrative examples of antibiotic components include, but are not limited to, minocycline hydrochloride and rifampin. The antibiotic components may be spray coated onto the materials using an L-tyrosine polymer. However, it to be understood that any suitable antibiotic, if desired, may be integrated with the prosthesis using other techniques as should be apparent to one of skill in the art.

In one embodiment, the prosthetic material may be coated or impregnated with one or more growth factors for a particular medical application. Any growth factors may be integrated with the prosthesis using any suitable technique as should be apparent to one of skill in the art.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. An implantable prosthesis for repairing a fistula, the fistula having a primary opening, a secondary opening and a fistula tract extending between the primary and secondary openings, the implantable prosthesis comprising:
   an implantable body of biocompatible material that is adapted to extend along and approximate the fistula tract, the body including first and second ends with a channel extending through the body to allow drainage of the fistula, the body including a plurality of layers of biocompatible material arranged in a stacked configuration with each layer being positioned in spaced relation to an adjacent layer;
   a first anchor located at the first end of the implantable body and adapted to be positioned at the primary opening of the fistula, the first anchor being larger than the implantable body; and
   a second anchor located at the second end of the implantable body and adapted to be positioned at the secondary opening of the fistula, the second anchor being larger than the implantable body.

2. The implantable prosthesis according to claim 1, wherein each of the first and second anchors includes at least one opening to allow drainage therethrough.

3. The implantable prosthesis according to claim 1, wherein
   the channel extends in a longitudinal direction and the body includes a plurality of lateral channels in communication with and extending in a lateral direction from the longitudinal channel.

4. The implantable prosthesis according to claim 1, wherein each layer includes at least one opening to allow drainage therethrough.

5. The implantable prosthesis according to claim 1, wherein the layers are fixed in position to maintain the spaced relation.

6. The implantable prosthesis according to claim 1, wherein adjacent layers are maintained in spaced relation by one or more spacers located between the adjacent layers.

7. The implantable prosthesis according to claim 1, wherein the layers are secured together with one or more sutures.

8. The implantable prosthesis according to claim 6, wherein the layers are secured together with one or more sutures and the spacers include one or more knots that are formed in the suture.

9. The implantable prosthesis according to claim 1, further comprising
   at least one tether extending from at least one of the first and second anchors and away from the body.

10. The implantable prosthesis according to claim 9, wherein at least one tether extends from each of the first and second anchors.

11. The implantable prosthesis according to claim 1, wherein the body has a tubular configuration.

12. The implantable prosthesis according to claim 1, wherein the body has an adjustable length to vary the distance between the first and second anchors.

13. The implantable prosthesis according to claim 1, wherein the body is adapted to support tissue ingrowth, revascularization and/or neovascularization.

14. The implantable prosthesis according to claim 1, wherein the first and second anchors are adapted to support tissue ingrowth, revascularization and/or neovascularization.

15. The implantable prosthesis according to claim 1, wherein the biocompatible material includes a biologic material.

16. The implantable prosthesis according to claim 1, wherein the biocompatible material is absorbable.

17. An implantable prosthesis for repairing a fistula, the fistula having a primary opening, a secondary opening and a fistula tract extending between the primary and secondary openings, the implantable prosthesis comprising:
   an implantable body of biocompatible material that is adapted to extend along and approximate the fistula tract, the body including first and second ends with a channel extending through the body to allow drainage of the fistula, the body has an adjustable length to vary the distance between the first and second anchors, the body including first and second body portions that are independent of each other and adjustable relative to each other to adjust the length, the first body portion being slidable within the second body portion;
   a first anchor located at the first end of the implantable body and adapted to be positioned at the primary opening of the fistula, the first anchor being larger than the implantable body; and
   a second anchor located at the second end of the implantable body and adapted to be positioned at the secondary opening of the fistula, the second anchor being larger than the implantable body.

18. The implantable prosthesis according to claim 17, wherein each of the first and second body portions has a tubular configuration.

19. The implantable prosthesis according to claim 17, wherein the first anchor is located at a first end of the first body portion and the second anchor is located at a second end of the second body portion.

20. An implantable prosthesis for repairing a fistula, the fistula having a primary opening, a secondary opening and a fistula tract extending between the primary and secondary openings, the implantable prosthesis comprising:
   an implantable body of biocompatible material that is adapted to extend along and approximate the fistula tract, the body including first and second ends with a channel extending through the body to allow drainage of the fistula, the body has an adjustable length to vary the distance between the first and second anchors, the body including first and second body portions that are independent of each other and adjustable relative to each other to adjust the length, the first and second body portions being arranged in a telescopic configuration;
   a first anchor located at the first end of the implantable body and adapted to be positioned at the primary opening of the fistula, the first anchor being larger than the implantable body; and
   a second anchor located at the second end of the implantable body and adapted to be positioned at the secondary opening of the fistula, the second anchor being larger than the implantable body.

* * * * *